(12) United States Patent
Liu (10) Patent No.: US 11,053,479 B2
(45) Date of Patent: Jul. 6, 2021

(54) MODIFIED TRANSFERRIN DNA BINDING DOMAIN, RECOMBINANT DNA POLYMERASE AND PREPARATION METHOD

(71) Applicant: FOREGENE COMPANY LIMITED, Chengdu (CN)

(72) Inventor: Huahua Liu, Chengdu (CN)

(73) Assignee: FOREGENE COMPANY LIMITED, Chengdu (CN)

( * ) Notice: Subject to any disclaimer, the term of this patent is extended or adjusted under 35 U.S.C. 154(b) by 0 days.

(21) Appl. No.: 16/301,738

(22) PCT Filed: Apr. 27, 2017

(86) PCT No.: PCT/CN2017/082154
§ 371 (c)(1),
(2) Date: Nov. 15, 2018

(87) PCT Pub. No.: WO2017/202172
PCT Pub. Date: Nov. 30, 2017

(65) Prior Publication Data
US 2019/0119356 A1    Apr. 25, 2019

(30) Foreign Application Priority Data

May 23, 2016    (CN) .......................... 201610345512.0

(51) Int. Cl.
*C12N 9/12*     (2006.01)
*C12N 15/00*    (2006.01)
(Continued)

(52) U.S. Cl.
CPC ............ *C12N 9/1252* (2013.01); *C07K 14/79* (2013.01); *C12N 9/1241* (2013.01); *C12N 15/62* (2013.01);
(Continued)

(58) Field of Classification Search
CPC .............................. C12N 9/1252; C07K 14/79
See application file for complete search history.

(56) References Cited

U.S. PATENT DOCUMENTS

2011/0091543 A1\*  4/2011  Prior ...................... A61K 38/26
                                                       424/463

FOREIGN PATENT DOCUMENTS

| WO | WO-9806860 A1 \* | 2/1998  | ............. A01N 63/10 |
| WO | 0134641 A2       | 5/2001  |                          |
| WO | 0172322 A2       | 10/2001 |                          |

OTHER PUBLICATIONS

Studer. Residue mutations and their impact on protein structure and function: detecting beneficial and pathogenic changes. Biochem. J. (2013) 449, 581-594.\*

(Continued)

*Primary Examiner* — Yong D Pak
(74) *Attorney, Agent, or Firm* — Bayramoglu Law Offices LLC (57) ABSTRACT

A modified transferrin DNA binding domain. The transferrin is lactotransferrin (LTF), serotransferrin (TF), melanotransferrin (MTF) or ovotransferrin (OTF), and the N terminal of each transferrin has one homologous DNA binding domain, wherein the $10^{th}$ site and $20^{th}$ site of the DNA binding domain are C; and the amino acid sequence of the modified transferrin DNA binding domain is as follows: C in the $10^{th}$ site and $20^{th}$ site is replaced by other amino acids so that no disulfide bond can be formed. The present invention also discloses a recombinant DNA polymerase and a preparation method thereof. The preparation method comprises the step of coupling the modified transferrin DNA binding domain (Continued)

with a DNA polymerase. The present invention also discloses a PCR test kit containing the recombinant DNA polymerase.

14 Claims, 3 Drawing Sheets

Specification includes a Sequence Listing.

(51) Int. Cl.
*C07K 14/00* (2006.01)
*C12N 15/62* (2006.01)
*C07K 14/79* (2006.01)
*C12Q 1/6876* (2018.01)

(52) U.S. Cl.
CPC .... *C12Q 1/6876* (2013.01); *C12Y 207/07007* (2013.01)

(56) References Cited

OTHER PUBLICATIONS

Metz-Boutigue. Human lactotransferrin: amino acid sequence and structural comparisons with other transferrins. Eur. J. Biochem. 145,659-676 (1984).*

Britigan. Lactoferrin Binds CpG-Containing Oligonucleotides and Inhibits Their Immunostimulatory Effects on Human B Cells. J Immunol 2001; 167:2921-2928.*

Oho. Functional Domain of Bovine Milk Lactoferrin Which Inhibits the Adherence of *Streptococcus mutans* Cells to a Salivary Film. Infection and Immunity, Sep. 2002, p. 5279-5282.*

Yan, W. et al., "A novel strategy to engineer DNA polymerases for enhanced processivity and improved performance in vitro", Nucleic Acids Research, vol. 32, No. 3, Feb. 18, 2004, ISSN: 0305-1048, see abstract.

Patrick, H.C. et al., "N-Terminal Stretch ARG2, ARG3, ARG4 and ARG5 of Human Lactoferrin is Essential for Binding to Heparin, Bacterial Lipopolysaccharide, Human Lysozyme and DNA", Biochemical J., vol. 328, Dec. 31, 1997, ISSN: 0021-924X, see abstract, the main body, p. 147, the right-hand column, the last paragraph.

Huo, L. J. et al., "Antimicrobial and DNA-binding activities of the peptide fragments of human lactoferrin and histatin 5 against *Streptococcus mutans*" Archives of Oral Biology, vol. 56, Dec. 31, 2011, ISSN: 0003-9969; see the whole document.

\* cited by examiner

MODIFIED TRANSFERRIN DNA BINDING DOMAIN, RECOMBINANT DNA POLYMERASE AND PREPARATION METHOD

CROSS REFERENCE TO RELATED APPLICATIONS

This application is the national phase entry of International Application No. PCT/CN2017/082154, filed on Apr. 27, 2017, which is based upon and claims priority to Chinese Patent Application No. 201610345512.0, filed on May 23, 2016, the entire contents of which are incorporated herein by reference.

TECHNICAL HELD

The present invention relates to the technical field of biology, and particularly relates to a modified transferrin DNA binding domain, a recombinant DNA polymerase and a preparation method.

BACKGROUND

Desoxyribonucleic acid (DNA) is a carrier for saving and transferring genetic information of lives, and DNA polymerase participating in desoxyribonucleic acid synthesis in a cell is a key molecule to realize autoduplication and genetic information transferring functions of DNA molecules. The development of biotechnology provides an in-vitro duplication method of DNA molecules, and the nucleic acid molecule testing technology developed hereby has increasingly become a key technology of various biological tests and is widely applied to theoretical researches and inspections such as drug development, food safety testing, pathogenic microorganism assay, disease mechanism and drug targeting.

The key to synthesize DNA molecules through the in-vitro enzymatic method is to obtain thermostable DNA polymerases for satisfying different needs, such as thermostable DNA polymerase for PCR amplification, thermostable DNA polymerase for resisting enzymeinhibitors, and thermostable DNA polymerase capable of amplify DNA at ultralow template concentration.

Nucleic acids in body fluid frequently need amplification testing in clinic in-vitro diagnosis, and many PCR reaction inhibitors exist in the body fluid, such as chlorhematin, calcium ion, hemoglobin, transferrin and immunoglobulin. These PCR reaction inhibitors prevent directly using the body fluid for PCR amplification, nucleic acid purification is usually needed to remove the PCR reaction inhibitors, and then the purified nucleic acids are used for PCR amplification.

Researches abroad show that the DNA binding domain of archaebacterianucleic acid binding protein and a thermostable DNA polymerase are recombined to construct a novelthermostable DNA polymerase which has higher infinity to templateDNA and keeps various functions of the original DNA polymerase. This recombinant DNA polymerase has the following characteristics: (1) the infinity to templateDNA molecules is greatly increased, and the recombinant DNA polymerase can be bound with the template DNA molecules at low concentration to initiate DNA synthesis; (2) the recombinant DNA polymerase with higher infinity to templateDNA molecules can initiate DNA synthesis in more complex reaction environment, such as in a solution of DNA primary products or original materials containing contaminants or interfering molecules; and (3) the recombinant DNA polymerase has obviously higher infinity to some segments of specific pathogen genome DNA and can initiate DNA synthesis at lower template concentration or in the presence of more complex interfering molecules. These characteristics can improve the process of nucleic acidtesting (to realize more simplified and large-scale operation) and increase testing sensitivity and stability. However, there are few recombinant DNA polymerases with the above advantages, so there is a pressing need to strengthen the research and development of recombinant DNA polymerases.

SUMMARY

The present invention needs to solve the technical problems of acquiring a novel recombinant DNA polymerase not easy to be inhibited by biomacromolecules (polysaccharide and protein), organic and inorganic contaminating molecules (compounds added to release DNA and denatured biomacromolecules), etc. to realize direct PCR; and acquiring a novel recombinant DNA polymerase with higher infinity to template molecules to realize amplification of templateat lower concentration and increase testing sensitivity and stability.

In order to solve the above technical problems, the present invention adopts the following technical scheme:

The present invention provides a modified transferrin DNA binding domain. The transferrin is lactotransferrin (LTF), serotransferrin (TF), melanotransferrin (MTF) or ovotransferrin (OTF), and the N terminal of each transferrin has one homologous DNA binding domain, wherein the $10^{th}$ site and $20^{th}$ site of the DNA binding domain are C; and the amino acid sequence of the modified transferrin DNA binding domain is as follows: C in the $10^{th}$ site and $20^{th}$ site is replaced by other amino acids so that no disulfide bond can be formed.

Furthermore, C in the $10^{th}$ site is replaced by R, and C in the $20^{th}$ site is replaced by A or G.

Furthermore, amino acids in the $1^{st}$ to $5^{th}$ sites of the DNA binding domain are replaced by KFKYK and/or amino acids in the $28^{th}$ to $31^{st}$ sites are replaced by KKVK.

Furthermore, the DNA binding domain of the lactotransferrin (LTF) is human-derived, as shown by SEQ ID No: 1, or mouse-derived, as shown by SEQ II) No: 2; the DNA binding domain of the serotransferrin (TF) is human-derived, as shown by SEQ ID No: 3, or mouse-derived, as shown by SEQ ID No: 4; the DNA binding domain of the melanotransferrin (MTF) is human-derived, as shown by SEQ ID No: 5, or mouse-derived, as shown by SEQ ID No: 6; and the DNA binding domain of the ovotransferrin (OTF) is chicken-derived, as shown by SEQ ID No: 7.

The present invention also provides a preparation method of a recombinant DNA polymerase, which comprises the step of coupling the modified transferrin DNA binding domain with a DNA polymerase to construct a recombinant DNA polymerase; or connecting identical DNA binding domains or different DNA binding domains in the modified transferrin DNA binding domain in series and then coupling with a DNA polymerase to construct a recombinant DNA polymerase; or mixing the constructed recombinant DNA polymerase with other recombinant DNA polymerases or unmodified DNA polymerases to obtain a compound recombinant DNA polymerase.

Furthermore, the DNA polymerase is thermostable DNA polymerase or reverse transcriptase.

Furthermore, the thermostable DNA polymerase is TaqDNApolymerase:

The present invention also provides a novel recombinant DNA polymerase prepared by the preparation method.

The present invention also provides a PCR test kit containing the recombinant DNA polymerase.

With the above technical scheme, the present invention at least has the following advantages:

A novel DNA binding domain namely transferrin DNA binding domain is obtained in the present invention, which can be coupled with a DNA polymerase to construct a recombinant DNA polymerase. The constructed recombinant DNA polymerase is not easy to be inhibited by biomacromolecules (polysaccharide and protein), organic and inorganic contaminating molecules (compounds added to release DNA and denatured biomacromolecules), etc. and can realize direct PCR. Thus, the testing procedure is simplified, the efficiency is improved, and operation is convenient. Meanwhile, the expense is reduced, the cost is lowered, the testing time is shortened, and the efficiency is increased. In addition, the constructed recombinant DNA polymerase has higher infinity to template molecules, can realize amplification of templateat lower concentration and increases testing sensitivity and stability.

BRIEF DESCRIPTION OF THE DRAWINGS

The technical scheme of the present invention is only described briefly above. To understand the technical means of the present invention more clearly, the present invention will now be described in more detail with reference to the appended drawings and embodiments.

DETAILED DESCRIPTION OF THE EMBODIMENTS

In order to acquire a novel DNA polymerase not easy to be inhibited and having low requirement for template concentration, the present invention chooses to construct a recombinant DNA polymerase through recombination. Lots of researches have shown that after replacing modification of partial amino acids, the transferrin DNA binding domain can be used for constructing a recombinant DNA polymerase with the above advantages.

Transferrin has four kinds of homologous proteins: lactotransferrin (LTF), serotransferrin (TF), melanotransferrin (MTF) and ovotransferrin (OTF). The N terminals of these four proteins have one homologous binding domain, wherein the $10^{th}$ and $20^{th}$ sites of the DNA binding domain are C.

Embodiment 1

In the embodiment, three human-derived, three mouse-derived and one chicken-derived transferrin DNA binding domains are detected, and the amino acid sequences are as follows respectively:

```
Human LTF (HLTF):
                                        (SEQ ID No: 1)
GRRRRSVQWCAVSQPEATKCFQWQRNMRKVR Human TF (HTF):
                                        (SEQ ID No: 3)
AVPDKTVRWCAVSEHEATKCQSFRDHMKSVI Human MTF (HMTF):
                                        (SEQ ID No: 5)
VLGGMEVRWCATSDPEQHKCGNMSEAFREAG Mouse LTF (MLTF):
                                        (SEQ ID No: 2)
LAKATTVQWCAVSNSEEEKCLRWQNEMRKVG Mouse TF (MTF):
                                        (SEQ ID No: 4)
AVPDKTVKWCAVSEHENTKCISFRDHMKTVL Mouse MTF (MMTF):
                                        (SEQ ID No: 6)
VVCVMEVQWCTISDAEQQKCKDMSEAFQGAG Chicken OTF (GOTF):
                                        (SEQ ID No: 7)
APPKSVIRWCTISSPEEKKCNNLRDLTQQER
```

A modification method of the above DNA binding domain is as follows:

There are two C amino acids in the transferrin DNA binding domain, which can form a disulfide bond which is unstable at high temperature. C in the $10^{th}$ site and $20^{th}$ site can be replaced by other amino acids, so that no disulfide bond can be formed. For example, preferably, C in the $10^{th}$ site of the fragment can be replaced by R, and C in the $20^{th}$ site can be replaced by two small amino acids A or C. This modified DNA binding domain can be directly coupled with a thermostable DNA polymerase to form a recombinant thermostable DNA polymerase.

The amino acid sequence of the modified transferrin DNA binding domain is as follows:

```
Human LTF' (HLTF'):
                                        (SEQ ID No: 8)
GRRRRSVQWRAVSQPEATKAFQWQRNMRKVR Human TF' (HTF'):
                                        (SEQ ID No: 9)
AVPDKTVRWRAVSEHEATKAQSFRDHMKSVI Human MTF' (HMTF'):
                                        (SEQ ID No: 10)
VLGGMEVRWRATSDPEQHKAGNMSEAFREAG Mouse LTF' (MLTF'):
                                        (SEQ ID No: 11)
LAKATTVQWRAVSNSEEEKALRWQNEMRKVG Mouse TF' (MTF'):
                                        (SEQ ID No: 12)
AVPDKTVKWRAVSEHENTKAISFRDHMKTVL Mouse MTF' (MMTF'):
                                        (SEQ ID No: 13)
VVCVMEVQWRTISDAEQQKAKDMSEAFQGAG Chicken OTF' (GOTF):
                                        (SEQ ID No: 14)
APPKSVIRWRTISSPEEKKANNLRDLIQQER
```

Embodiment 2

The transferrin DNA binding domain obtained in the embodiment 1 can be further modified. Amino acids in the $1^{st}$ to $5^{th}$ sites of the transferrin DNA binding domain are replaced by KFKYK, and amino acids in the $28^{th}$ to $31^{st}$ sites are replaced by KKVK, wherein the modification of amino acids in the $1^t$ to $5^{th}$ sites is relatively important. The properties of the DNA polymerase can be further improved.

The amino acid sequence of the transferrin DNA binding domain modified in the second step is as follows:

```
Human LTF" (HLTF"):
                                         (SEQ ID No: 15)
KFKYKSVQWRAVSQPEATKAFQWQRNMKKVK Human TF" (HTF"):
                                         (SEQ ID No: 16)
KFKYKTVRWRAVSEHFATKAQSFRDHMKKVK Human MTF" (HMTF"):
                                         (SEQ ID No: 17)
KFKYKEVRWRATSDPEQHKAGNMSEAFKKVK Mouse LTF" (MLTF"):
                                         (SEQ ID No: 18)
KFKYKTVQWRAVSNSEEEKALRWQNEMKKVK Mouse TF" (MTF"):
                                         (SEQ ID No: 19)
KFKYKTVKWRAVSEHENTKAISFRDHMKKVK Mouse MTF" (MMTF"):
                                         (SEQ ID No: 20)
KFKYKEVQWRTISDAEQQKAKDMSEAFKKVK Chicken OTF" (GOTF"):
                                         (SEQ ID No: 21)
KFKYKVIRWRTISSPEEKKANNLRDLTKKVK
```

Embodiment 3

The transferrin DNA binding domains modified in the embodiments 1 and 2 are coupled with TaqDNA polymerase to form a recombinant thermostable DNA polymerase.

Figure 1:
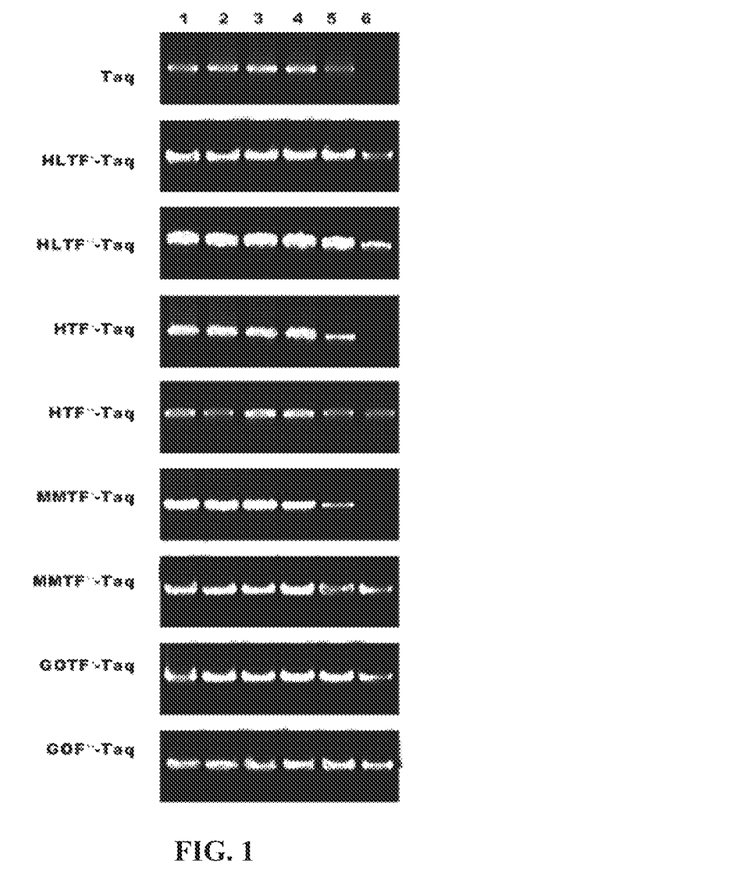
FIG. 1 is a comparison result diagram between the amplification efficiency of the recombinant thermostableDNA polymerase and that of TaqDNA polymerase in the embodiment 3.

(I) Amplification efficiency comparison experiment:

Dilute purified Taq, HLTF'-Taq, HLTF"-Taq, HTF'-Taq, HTF"-Taq, MMTF'-Taq, MMTF"-Taq, GOTF'-Taq and GOTF"-Taq continuously in a half-and-half way, take at each dilution degree, and amplify to 1.5 kb DNA fragments (25 cycles) in 20 µL reaction volume. FIG. 1, shows the amplification results of Taq with equal zymoprotein concentration in agarose gel electrophoresis lanes 1-6 (loading 5 µl/lane) or recombinant thermostable DNA polymerase after continuous dilution in a half-and-half way (1, ½, ¼, ⅛, ¹⁄₁₆, ¹⁄₃₂).

Figure 2:
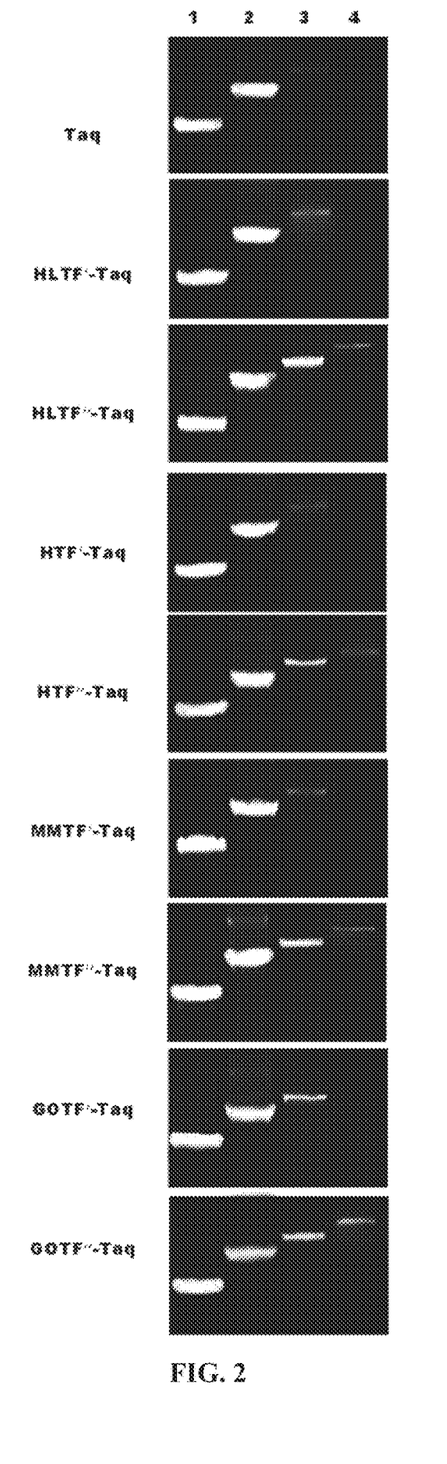
FIG. 2 is a comparison result diagram between the amplification speed of the recombinant thermostableDNA polymerase and that of TaqDNA polymerase in the embodiment 3.

(2) Amplification speed comparison experiment: as shown in FIG. 2, Taq, HLTF'-Taq, HLTF"-Taq, HTF'-Taq, HTF"-Taq, MMTF'-Taq, MMTF"-Taq, GOTF'-Taq and GOTF"-Taq amplify to 1.5 kb, 2.5 kb, 3.5 kb and 4.5 kb DNA fragments within extended 20 s conditions.

Experimental results show that the recombinant thermostable DNA polymerase has higher amplification efficiency (as shown in FIG. 1) and quicker amplification speed (as shown in FIG. 2) than the TaqDNApolymerase.

(3) Serum tolerance comparison experiment

Figure 3:
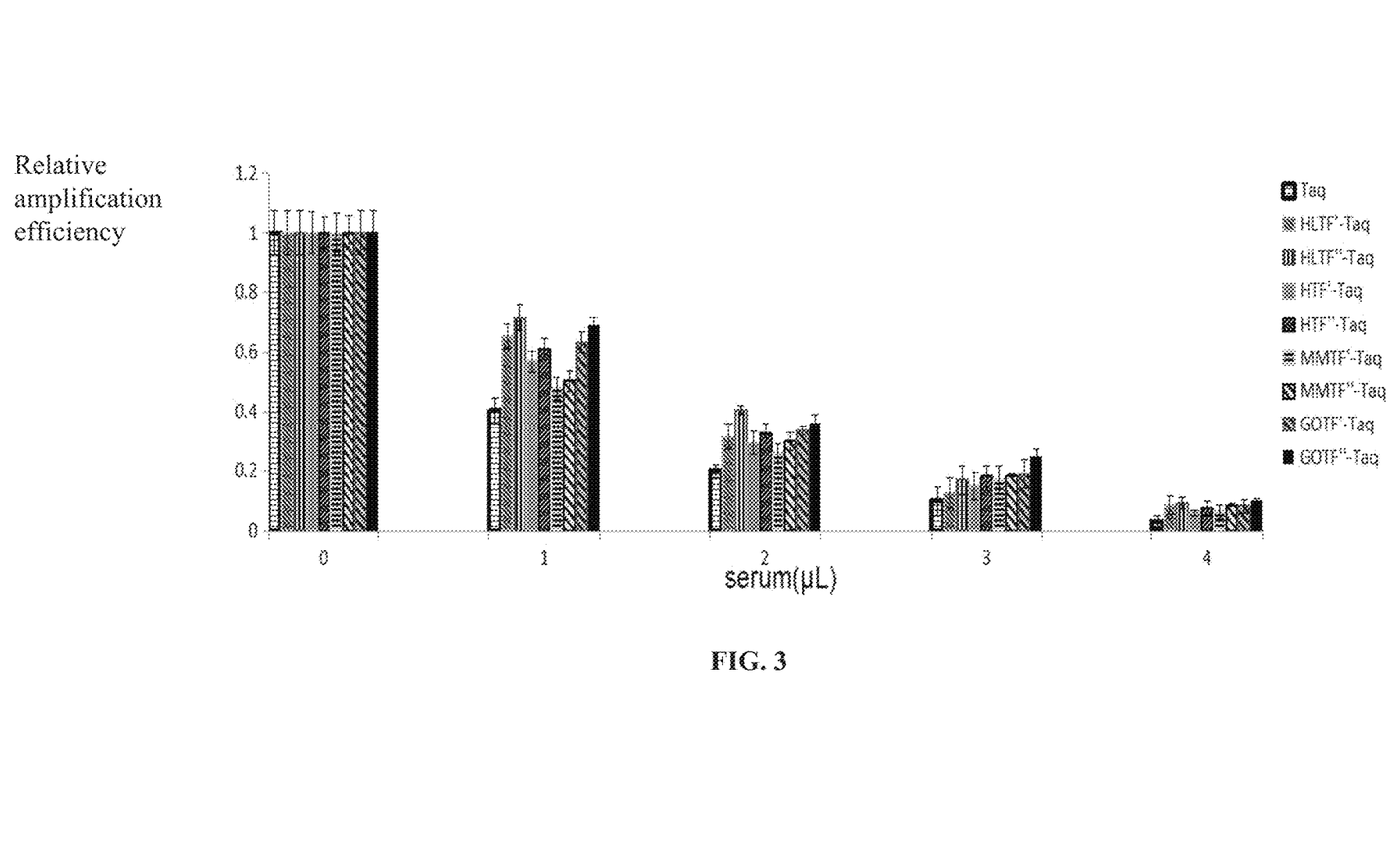
FIG. 3 is a comparison result diagram between the serum tolerance of the recombinant thermostableDNA polymerase and that of TaqDNA polymerase in the embodiment 3.

Prepare a certain quantity of PCR reaction system (SYBR Green) from Taq, HLTF'-Taq, Huff"-Taq, HTF'-Taq, HTF"-Taq, MMTF'-Taq, MMTF"-Taq, GOTF'-Taq and GOTF"-Taq, and add PCV2 DNA virus particles ($10^3$ PCV2 particles/Reaction), PCV2 primer and different quantities of pig serum (each 0, 1, 2, 3, 4 µL of pig serum in total 20 µl of qPCR solution) for PCR amplification. The amplification efficiency of the samples with serum added (1-4 µL) is obviously lower than that of the sample without serum added (0 µL), and the samples using the recombinant thermostable DNA polymerase and Taq for amplification have obvious difference in lowering speed. (As shown in FIG. 3), the experimental results show that the recombinant thermostable DNA polymerase has higher serum tolerance than the TaqDNApolymerase.

Embodiment 4

The transferrin DNA binding domains modified in the embodiments 1 and 2 are coupled with reverse transcriptase to form recombinant reverse transcriptase. Through RT-PCR experiment analysis, the amplification efficiency comparison experiment, amplification speed comparison experiment and serum tolerance comparison experiment similar to the embodiment 3 yield similar results, namely higher amplification efficiency, quicker amplification speed and higher serum tolerance.

Embodiment 5

Identical DNA binding domains in the transferrin DNA binding domains modified in the embodiments 1 and 2 are connected in series and then coupled with a DNA polymerase to construct a recombinant DNA polymerase; or different DNA binding domains in the transferrin DNA binding domains modified in the embodiments 1 and 2 are connected in series and then coupled with a DNA polymerase to construct a recombinant DNA polymerase. Both modes can yield similar experimental results, namely higher amplification efficiency, quicker amplification speed and higher serum tolerance.

In addition, the recombinant DNA polymerases constructed in the embodiments 1 and 2 or the above recombinant DNA polymerases constructed in this embodiment can be mixed with other recombinant DNA polymerases in the prior art or unmodified DNA polymerases to obtain a compound DNA polymerase. Compared with ordinary DNA polymerases, the compound DNA polymerase also has the advantages of higher amplification efficiency, quicker amplification speed and higher serum tolerance.

Finally, it should be noted that the $10^{th}$ and $20^{th}$ sites in the present invention are not fixed positions, amino acids corresponding to these two positions are C, and the two C differ by 10 amino acids, and the rest $1^{st}$ to $5^{th}$ sites and $28^{th}$ to $31^{st}$ sites are positions relative to the $10^{th}$ site. That is to say, for one DNA binding domain containing 40 amino acids, two amino acids are C and differ by 10 amino acids, and the positions corresponding to these two amino acids are determined as the $10^{th}$ and $20^{th}$ sites.

It should be noted that these drawings depict only preferable embodiments of the present invention and therefore should not be considered as limiting the scope of the present invention. Some simple amendments, equivalent changes or modifications made by those skilled in the art based on the above technical content fall within the scope of the present invention.

What is claimed is:

1. A modified DNA binding domain, wherein: the modified DNA binding domain is modified from a homologous DNA binding domain of a transferrin, wherein the transferrin is selected from the group consisting of lactotransferrin (LTF), serotransferrin (TF), melanotransferrin (MTF) and ovotransferrin (OTF), and wherein the modified DNA binding domain comprises an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7 except that,
the Cys residue at position 10 and the Cys residue at position 20 are replaced with a different amino acid so that no disulfide bond is formed between the amino acid at position 10 and the amino acid at position 20.

2. The modified DNA binding domain according to claim 1, wherein: the Cys residue at position 10 is replaced with an Arg residue and the Cys residue at position 20 is replaced with an Ala or Gly residue.

3. The modified DNA binding domain according to claim 1, wherein the modified DNA binding domain further differs from SEQ ID NO:1-7, in that the amino acids at positions 1-5 are replaced with KFKYK and/or the amino acids at positions 28-31 are replaced with KKVK.

4. A method of producing a recombinant DNA polymerase, comprising a step of linking the modified DNA binding domain of claim 1 with a DNA polymerase to construct a first recombinant DNA polymerase; or linking identical modified DNA binding domains or different modified DNA binding domains of claim 1 in series and then linking with a DNA polymerase to construct a second recombinant DNA polymerase.

5. The method according to claim 4, wherein: the DNA polymerase is thermostable DNA polymerase or reverse transcriptase.

6. The method according to claim 5, wherein: the thermostable DNA polymerase is Taq DNA polymerase.

7. The recombinant DNA polymerase prepared by the method of claim 4.

8. A PCR test kit, containing the recombinant DNA polymerase of claim 7.

9. The modified DNA binding domain according to claim 2, wherein the modified DNA binding domain further differs from SEQ ID NO:1-7, in that the amino acids at positions 1-5 are replaced with KFKYK and/or the amino acids at positions 28-31 are replaced with KKVK.

10. The method according to claim 4, wherein the amino acid at position 10 of the modified binding domain is replaced with an Arg residue and the amino acid at position 20 of the modified binding domain is replaced with an Ala residue or a Gly residue.

11. The method according to claim 4, wherein the modified DNA binding domain further differs from SEQ ID NO:1-7, in that the amino acids at positions 1-5 are replaced with KFKYK and/or the amino acids at positions 28-31 are replaced with KKVK.

12. The recombinant DNA polymerase according to claim 7, wherein the DNA polymerase is thermostable DNA polymerase or reverse transcriptase.

13. The recombinant DNA polymerase according to claim 7, wherein the thermostable DNA polymerase is Taq DNA polymerase.

14. The modified DNA binding domain according to claim 1, wherein the modified DNA binding domain comprises an amino acid sequence selected from the group consisting of SEQ ID NO:8, SEQ ID NO:9, SEQ ID NO:10, SEQ ID NO:11, SEQ ID NO:12, SEQ ID NO:13, and SEQ ID NO:14.

* * * * *

SEQUENCE LISTING

<160> NUMBER OF SEQ ID NOS: 21

<210> SEQ ID NO 1
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 1

Gly Arg Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Val Arg
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 2

Leu Ala Lys Ala Thr Thr Val Gln Trp Cys Ala Val Ser Asn Ser Glu
1               5                   10                  15

Glu Glu Lys Cys Leu Arg Trp Gln Asn Glu Met Arg Lys Val Gly
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 3

Ala Val Pro Asp Lys Thr Val Arg Trp Cys Ala Val Ser Glu His Glu
1               5                   10                  15

Ala Thr Lys Cys Gln Ser Phe Arg Asp His Met Lys Ser Val Ile
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 4

Ala Val Pro Asp Lys Thr Val Lys Trp Cys Ala Val Ser Glu His Glu
1               5                   10                  15

Asn Thr Lys Cys Ile Ser Phe Arg Asp His Met Lys Thr Val Leu
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

```
<400> SEQUENCE: 5

Val Leu Gly Gly Met Glu Val Arg Trp Cys Ala Thr Ser Asp Pro Glu
1               5                   10                  15

Gln His Lys Cys Gly Asn Met Ser Glu Ala Phe Arg Glu Ala Gly
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 6

Val Val Cys Val Met Glu Val Gln Trp Cys Thr Ile Ser Asp Ala Glu
1               5                   10                  15

Gln Gln Lys Cys Lys Asp Met Ser Glu Ala Phe Gln Gly Ala Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: The sequence is a synthesized amino acid
      sequence of a chicken-derived transferrin DNA binding domain

<400> SEQUENCE: 7

Ala Pro Pro Lys Ser Val Ile Arg Trp Cys Thr Ile Ser Ser Pro Glu
1               5                   10                  15

Glu Lys Lys Cys Asn Asn Leu Arg Asp Leu Thr Gln Gln Glu Arg
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 8

Gly Arg Arg Arg Ser Val Gln Trp Arg Ala Val Ser Gln Pro Glu
1               5                   10                  15

Ala Thr Lys Ala Phe Gln Trp Gln Arg Asn Met Arg Lys Val Arg
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 9

Ala Val Pro Asp Lys Thr Val Arg Trp Arg Ala Val Ser Glu His Glu
1               5                   10                  15

Ala Thr Lys Ala Gln Ser Phe Arg Asp His Met Lys Ser Val Ile
            20                  25                  30

<210> SEQ ID NO 10
<211> LENGTH: 31
```

```
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 10

Val Leu Gly Gly Met Glu Val Arg Trp Arg Ala Thr Ser Asp Pro Glu
1               5                   10                  15

Gln His Lys Ala Gly Asn Met Ser Glu Ala Phe Arg Glu Ala Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 11

Leu Ala Lys Ala Thr Thr Val Gln Trp Arg Ala Val Ser Asn Ser Glu
1               5                   10                  15

Glu Glu Lys Ala Leu Arg Trp Gln Asn Glu Met Arg Lys Val Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 12

Ala Val Pro Asp Lys Thr Val Lys Trp Arg Ala Val Ser Glu His Glu
1               5                   10                  15

Asn Thr Lys Ala Ile Ser Phe Arg Asp His Met Lys Thr Val Leu
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 13

Val Val Cys Val Met Glu Val Gln Trp Arg Thr Ile Ser Asp Ala Glu
1               5                   10                  15

Gln Gln Lys Ala Lys Asp Met Ser Glu Ala Phe Gln Gly Ala Gly
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: The sequence is a synthesized amino acid
      sequence of a chicken-derived transferrin DNA binding domain

<400> SEQUENCE: 14

Ala Pro Pro Lys Ser Val Ile Arg Trp Arg Thr Ile Ser Ser Pro Glu
1               5                   10                  15
```

Glu Lys Lys Ala Asn Asn Leu Arg Asp Leu Thr Gln Gln Glu Arg
             20                  25                  30

<210> SEQ ID NO 15
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 15

Lys Phe Lys Tyr Lys Ser Val Gln Trp Arg Ala Val Ser Gln Pro Glu
1               5                   10                  15

Ala Thr Lys Ala Phe Gln Trp Gln Arg Asn Met Lys Lys Val Lys
             20                  25                  30

<210> SEQ ID NO 16
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 16

Lys Phe Lys Tyr Lys Thr Val Arg Trp Arg Ala Val Ser Glu His Glu
1               5                   10                  15

Ala Thr Lys Ala Gln Ser Phe Arg Asp His Met Lys Lys Val Lys
             20                  25                  30

<210> SEQ ID NO 17
<211> LENGTH: 31
<212> TYPE: PRT
<213> ORGANISM: Artificial Sequence
<220> FEATURE:
<223> OTHER INFORMATION: The sequence is a synthesized amino acid
      sequence of a human-derived transferrin DNA binding domain

<400> SEQUENCE: 17

Lys Phe Lys Tyr Lys Glu Val Arg Trp Arg Ala Thr Ser Asp Pro Glu
1               5                   10                  15

Gln His Lys Ala Gly Asn Met Ser Glu Ala Phe Lys Lys Val Lys
             20                  25                  30

<210> SEQ ID NO 18
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 18

Lys Phe Lys Tyr Lys Thr Val Gln Trp Arg Ala Val Ser Asn Ser Glu
1               5                   10                  15

Glu Glu Lys Ala Leu Arg Trp Gln Asn Glu Met Lys Lys Val Lys
             20                  25                  30

<210> SEQ ID NO 19
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

```
<400> SEQUENCE: 19

Lys Phe Lys Tyr Lys Thr Val Lys Trp Arg Ala Val Ser Glu His Glu
1               5                   10                  15

Asn Thr Lys Ala Ile Ser Phe Arg Asp His Met Lys Lys Val Lys
                20                  25                  30

<210> SEQ ID NO 20
<211> LENGTH: 31
<212> TYPE: PRT
<213> ORGANISM: Artificial Sequence
<220> FEATURE:
<223> OTHER INFORMATION: The sequence is a synthesized amino acid
      sequence of a mouse-derived transferrin DNA binding domain

<400> SEQUENCE: 20

Lys Phe Lys Tyr Lys Glu Val Gln Trp Arg Thr Ile Ser Asp Ala Glu
1               5                   10                  15

Gln Gln Lys Ala Lys Asp Met Ser Glu Ala Phe Lys Lys Val Lys
                20                  25                  30

<210> SEQ ID NO 21
<211> LENGTH: 31
<212> TYPE: PRT
<213> ORGANISM: Artificial Sequence
<220> FEATURE:
<223> OTHER INFORMATION: The sequence is a synthesized amino acid
      sequence of a chicken-derived transferrin DNA binding domain

<400> SEQUENCE: 21

Lys Phe Lys Tyr Lys Val Ile Arg Trp Arg Thr Ile Ser Ser Pro Glu
1               5                   10                  15

Glu Lys Lys Ala Asn Asn Leu Arg Asp Leu Thr Lys Lys Val Lys
                20                  25                  30
```